US007625562B2

(12) United States Patent
El Haj et al.

(10) Patent No.: US 7,625,562 B2
(45) Date of Patent: Dec. 1, 2009

(54) GENERATION OF CARTILAGE USING MAGNETIZABLE PARTICLES

(75) Inventors: Alicia Jennifer Hafeeza El Haj, Stoke-on-Trent (GB); Jon Paul Dobson, Stoke-on-Trent (GB)

(73) Assignee: Keele University, Staffordshire (GB)

( * ) Notice: Subject to any disclaimer, the term of this patent is extended or adjusted under 35 U.S.C. 154(b) by 28 days.

(21) Appl. No.: 10/518,956

(22) PCT Filed: Jun. 19, 2003

(86) PCT No.: PCT/GB03/02624

§ 371 (c)(1),
(2), (4) Date: Aug. 10, 2005

(87) PCT Pub. No.: WO04/000369

PCT Pub. Date: Dec. 31, 2003

(65) Prior Publication Data

US 2006/0093611 A1    May 4, 2006

(30) Foreign Application Priority Data

Jun. 19, 2003    (GB) ................. 0214209.9

(51) Int. Cl.
*A61K 39/00* (2006.01)
*A61K 33/26* (2006.01)
*G11B 5/708* (2006.01)
*A61N 2/00* (2006.01)
(52) U.S. Cl. ................. 424/178.1; 424/646; 428/842.2; 600/9; 600/12; 600/14; 977/904; 977/906
(58) Field of Classification Search ....................... None
See application file for complete search history.

(56) References Cited

U.S. PATENT DOCUMENTS

2004/0147015 A1    7/2004   El Haj

FOREIGN PATENT DOCUMENTS

| WO | WO 95/06248 A1 | 3/1995 |
|---|---|---|
| WO | WO 01/88540 A1 | 11/2001 |
| WO | WO 02/051985 A2 | 7/2002 |

OTHER PUBLICATIONS

O'Grady et al., Molecular diversity and function of voltage-gated (Kv) potassium channels in epithelial cells, 2005, The International Journal of Biochemistry and Cell Biology, vol. 37, pp. 1578-1594.*
Yanase et al., Intracellular hyperthermia for cancer using magnetite cationic liposomes: Ex vivo study, 1997, Japanese Journal of Cancer Research, vol. 88, pp. 630-632.*
Yanase et al., Intracellular hyperthermia for cancer using magnetite cationic liposomes: an in vivo study, 1998, Japanese Journal of Cancer Research, vol. 89, pp. 463-469.*
Ito et al., Medical Application of functionalized magnetic nanoparticles, 2005, Journal of Bioscience and Bioengineering, vol. 100, pp. 1-11.*
Komarova et al., Osteoclast ion channels: potential targets for antiresportive drugs, 2001, Current Pharmaceutical Design, vol. 7, pp. 637-654.*
Ullrich et al., Expression of voltage-activated chloride currents in acute slices of human gliomas, 1998, Neuroscience, vol. 83, Issue 4, pp. 1161-1173.*
Cartmell et al., "Development of Magnetic Particle Techniques for Long-Term Culture of Bone Cells With Intermittent Mechanical Activation," *IEEE Trans. Nanobiosci.* 1:92-97 (2002).
Cartmell et al., "Preliminary Analysis of Magnetic Particle Techniques for Activating Mechanotransduction in Bone Cells," *IEEE*, pp. 87-88 (2002).
Glogauer et al., "Magnetic Fields Applied to Collagen-Coated Ferric Oxide Beads Induce Stretch-Activated $Ca^{2+}$ Flux in Fibroblasts," *Am. J. Physiol.* 269:C1093-C1104 (1995).
Dobson and St. Pierre, "Application of the Ferromagnetic Transduction Model to D.C. and Pulsed Magnetic Fields: Effects on Epileptogenic Tissue and Implications for Cellular Phone Safety," *Biochem. Biophys. Res. Comm.* 227:718-723 (1996).
Dobson and El Haj, "Theoretical Evaluation of the Magnetic Force Bioreactor," Internet Article, 'Online! XP002257583, Retrieved from the Internet: <URL:http://www.maths.nottingham.ac.uk/Cmm/MMSG2001/SGprobsInf.html>, retrieved on Jul. 31, 2001, Abstract.
Mykhaylyk et al., "Signal Transduction of Erythrocytes After Specific Binding of Ecdysterone and Cholesterol Immobilized on Nanodispersed Magnetite," *J. Magn. Magn. Mater.* 225:226-234 (2001).
Schütt et al., "Applications of Magnetic Targeting in Diagnosis and Therapy—Possibilities and Limitations: A Mini-Review," *Hybridoma* 16:109-117 (1997).
Yang, Ying et al., "Development of a 'mechano-active' scaffold for tissue engineering." Biomaterials, vol. 23 pp. 2119-2126 (2002).
Santra, Swadeshmukul, "Synthesis and Characterization of Silica-Coated Iron Oxide Nanoparticles in Microemulsion: The Effect of Nonionic Surfactants," vol. 17 pp. 2900-2906 (2001).
Hughes, Steven, et al. "Magnetic targeting of mechanosensors in bone cells for tissue engineering applications." Journal of Biomechanics, vol. 40 (2007) pp. S96-S104.

(Continued)

*Primary Examiner*—Robert Landsman
*Assistant Examiner*—Ian Dang
(74) *Attorney, Agent, or Firm*—Janet Sleath; Speckman Law Group PLLC

(57) ABSTRACT

There is described a method of magnetically manipulating a cell in vivo which comprises the association of a magnetizable particle with a cell. More particularly, there is described a method of magnetically manipulating a cell which comprises the association of a magnetizable particle with a cell characterized in that the method comprises agonizing or antagonizing ion channels within a cell by the association of a magnetizable particle with a cell. There is also described the use of a magnetizable particle in a method of magnetically manipulating a cell in vivo and/or activating ion channels in vivo.

19 Claims, 4 Drawing Sheets

OTHER PUBLICATIONS

Cartmell, Sarah H., et al. "'Development of Magnetic Particle Techniques for Long-Term Culture of Bone Cells with Intermittent Mechanical Activation." IEEE Transactions on Nanobioscience, vol. 1 No. 2 (2002) pp. 92-97.

Dobson, Jon, et al. "Principles and Design of a Novel Magnetic Force Mechanical Conditioning Bioreactor for Tissue Engineering, Stem Cell Conditioning, and Dynamic in Vitro Screening." IEEE Transactions on Nanobioscience, vol. 5 No. 3 (2006) pp. 173-177.

Hughes, Steven, et al. "Expression of the Mechanosensitive 2PK+ Channel TREK-1 in Human Osteoblasts." Journal of Cellular Physiology, vol. 206 pp. 738-748 (2006).

Hughes, Steven, et al. "Selective activation of mechanosensitive ion channels using magnetic particles." J.R. Society Interface, vol. 5 pp. 855-863 (2008).

Wolbank, S., et al. "In vivo tracking of stem cells using magnetic tagging in a nude mouse model" Journal of Biomechanics, vol. 39 pp. S447 (2006).

El Haj, A.J., et al. "Magnetic nanoparticle-based tagging of mechanosensors for bone tissue engineering." Journal of Biomechanics, vol. 39 pp. S214 (2006).

Wang, J., et al., "Force regulates smooth muscle actin in cardiac fibroblasts," Am J. Physiol Heart Circ Physiol, vol. 279, pp. H2776-2785 (2000).

Maingret, Francois, et al., "Mechano- or Acid Stimulation, Two Interactive Modes of Activation of the TREK-1 Potassium Channel," The Journal of Biological Chemistry, vol. 274, No. 38, pp. 26691-26696 (Sep. 17, 1999).

Laniado, Marc E., et al., "Voltage-Gated K+ Channel Activity in Human Prostate Cancer Cell Lines of Markedly Different Metastatic Potential: Distinguishing Characteristics of PC-3 and LNCaP Cells," The Prostate, vol. 46, pp. 262-274 (2001).

Mitsugu, Yanase, et al., "Intracellular Hyperthermia for Cancer Using Magnetite Cationic Liposomes: An in vivo Study." Jpn. J. Cancer Res. vol. 89, pp. 463-469 (Apr. 1998).

* cited by examiner

Figure 2 : Magnetic activation of Trek-1 monitored via downstream changes in intracellular calcium

- COS-7 cells cotransfected with 'Flash' pericam and 12His.Trek-1 – Red and yellow lines indicate the cells with magnetic particles attached. Green and White lines indicate the cells without magnetic particles attached.
- Magnetic field applied for 1 sec – yellow arrow.
- Application of 100uM Riluzole to the culture media – red arrow

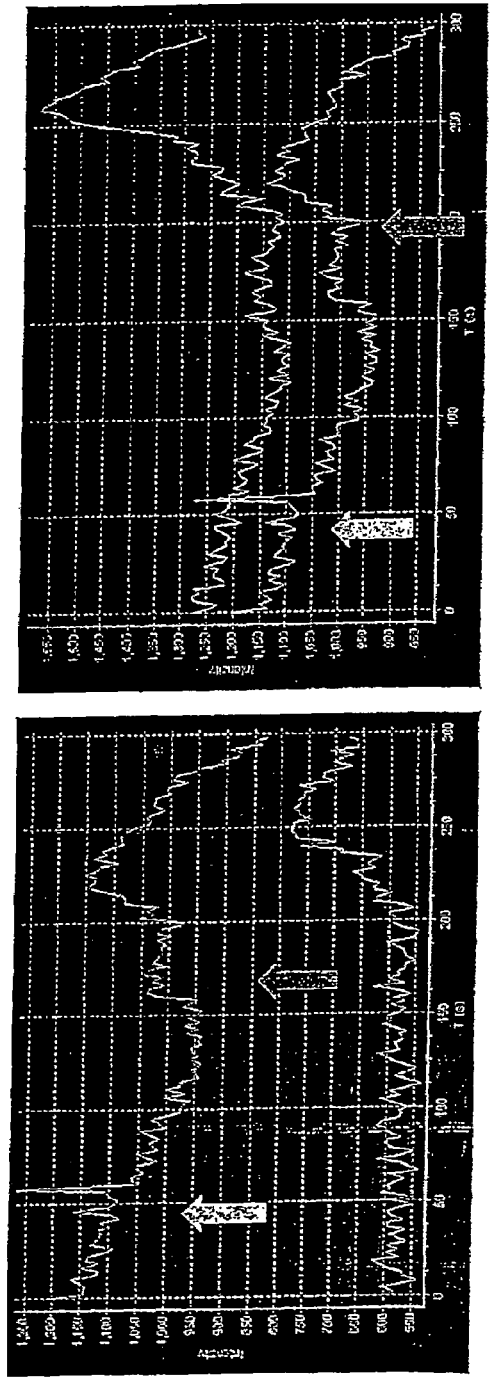

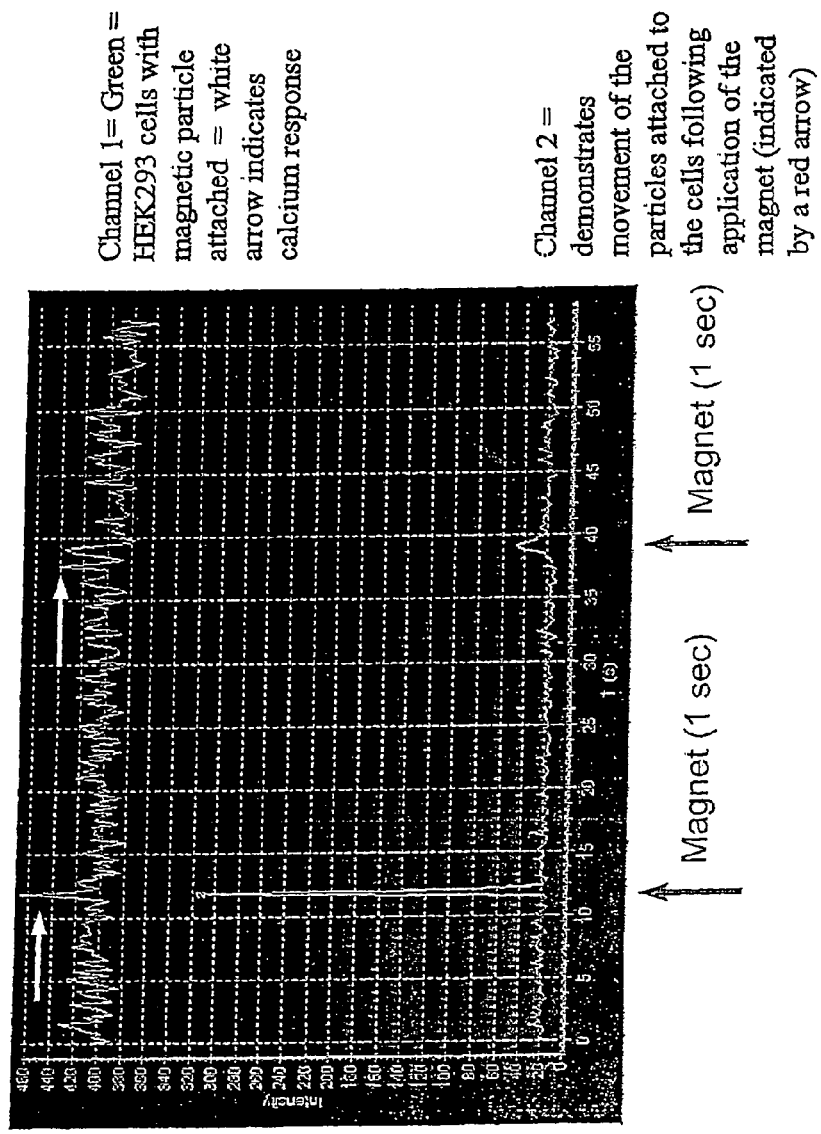
Figure 3 : Magnetic activation of TREK-1 induces transient rise in intracellular calcium in HEK293 T cells co-transfected with and Flashpericam

GENERATION OF CARTILAGE USING MAGNETIZABLE PARTICLES

CROSS REFERENCE TO RELATED APPLICATIONS

This is a § 371 application of PCT/GB2003/002624 filed Jun. 19, 2003, which claims the benefit of Great Britain Application No. 0214209.9 filed Jun. 19, 2002.

FIELD OF THE INVENTION

This invention relates to a novel method of magnetically manipulating cells in vivo and to methods of treatment related thereto.

BACKGROUND OF THE INVENTION

It is well established in pharmacology that communication, e.g. between cells, is governed by ion channels within the cells. A wide variety of such channels exist for example potassium, calcium and sodium channels. Pharmaceutically active chemical compounds are often used to block such channels resulting in a pharmacological effect. For example, calcium antagonists are known to be active on the cardiovascular system, for example by reducing the magnitude of the calcium current in the sino-atrial and atrio ventricular nodes. An important aspect of ion channel control is determining when the channel opens (gating).

Ion channels generally possess ionic selectivity which is an extremely important aspect of the channel's functional properties. Channels are generally characterised by their ionic selectivity, for example sodium channel
potassium channel
calcium channel
chloride channel
non-selective cation channel.

Ion channels are large integral membrane proteins that form pores through a cellular plasma membrane allowing ions to cross by flowing down an electrochemical gradient through the channels passive transport). The core of the pore is generally hydrophilic, and contains a part of the protein which recognises only certain ions thus acting as a selectivity filter. Gates in the channel can open in response to a variety of stimuli, including changes in membrane potential, mechanical activation or the presence of certain chemicals outside or inside the cell. More than 50 types of ion channels have been identified.

Ca channels, like Na channels, are voltage-gated, open when the internal voltage becomes more positive than the resting potential, and inactivate, or close, spontaneously even though the voltage stimulus is maintained. Ca channels are effective in the axon terminals of neurons, and in invertebrate muscle, vertebrate smooth muscle, and participate with Na channels in vertebrate cardiac muscle. Ca++ channels participate in action potentials when you need to get Ca++ into the cell to do something, such as make cardiac muscle contract, or release neurotransmitter at the axon terminal.

Na channels are almost all voltage-gated, that is, their gates open in response to changes in membrane potential, usually when the inside of the cell becomes more positive. Most Na channels are closed, or inactivate, spontaneously in a few milliseconds even though the membrane potential remains at the level which opened them. Na channels are found in neurons, vertebrate skeletal muscle, and cardiac muscle. Na serves to let charge into the cell; the Na itself doesn't do anything chemically.

Potassium channels, like Na channels, tend to be voltage-gated and to open when the inside of the cells becomes more positive. They mostly open at voltage more positive than Na or Ca channels, and most of them stay open as long as the voltage stays positive. Since the Nernst potential for K is near −80 mV, opening K channels at voltages near +20 mV lets K out and makes the internal voltage more negative. This in turn closes the K channels. This is how the action potential repolarises, or returns to resting potential. There are also K channels that are not voltage-gated. These are open at the resting potential, and in fact set the resting potential.

U.S. Pat. No. 6,548,264 describes silica coated nanoparticles which comprise a magnetic metal core. The magnetic core present in the particles enables the particles to be responsive to a magnetic field and therefore, the particles are suitable for use in diagnostic, imaging and recording systems. However, the nanoparticles of the prior art may suffer from the disadvantage that hey do not define the method of activation at a cellular level.

Magnetic bead twisting cytometry has been used to define the mechanical properties of single cells and to demonstrate that external mechanical forces can be transmitted across the cell surface and through the cytoskeleton via transmembrane cell adhesion molecules such as integrins, see, for example, Wang, N and Ingberger, DE (1995) Probing transmembrane mechanical coupling and cytomechanics using magnetic twisting cytometry. *Biochem Cell Biol.* 73: 327-335.

We have now found a method of selectively activating cells which enables the cells to then be manipulated mechanically in a remote manner, e.g. from outside the body.

Thus according to the invention we provide a method of magnetically manipulating a cell in vivo which comprises the association of a magnetisable particle with a cell.

The method may comprise ex vivo manipulation of an in vivo process. Furthermore, it will be understood by the skilled man that a reference to a cell shall be construed to include a plurality of cells.

More particularly, the invention provides a method of agonising or antagonising ion channels within a cell which comprises the association of a magnetisable particle with a cell as hereinbefore described.

According to a further aspect of the invention we provide a method of magnetically manipulating a cell which comprises the association of a magnetisable particle with a cell characterised in that the method comprises agonising or antagonising ion channels within a cell by the association of a magnetisable particle with a cell.

SUMMARY O FTHE INVENTION

In this aspect of the invention the magnetisable particle may be associated directly with the cell. Alternatively, the method may comprise associating the magnetisable particle with an antibody, enzyme, etc., which is subsequently associated with the cell.

The association of a magnetisable particle with a cell may comprise the introduction of such a particle into a cell, the attachment of such a particle to a cell, e.g. externally or internally to a cell, or any combination thereof. Thus, the magnetisable particles may be associated intracellularly or extracellularly or a combination of intracellularly and extracellularly. However, in a preferred aspect of the invention the particles are associated intracellularly.

When the method of the invention comprises intracellular association this will comprise association with an internal binding site. By way of example only, for TREK-1, the particle(s) may be associated with the N-terminus region of the ion channel. Alternatively, the particle (s) may be associated with the COOH terminus region of the ion channel. It will be appreciated by one skilled in the art that numerous ion channels and binding sites may be utilised in the method of the invention. Thus, internal binding sites which correspond to the N-terminus region of the ion channel, as seen in TREK-1 or which corresponds to the COOH terminus region of the ion channel as seen in TREK-1 may be utilised as well as other binding sites known per se.

Thus, we also provide a method of manipulating a mechanosensitive ion channel characterised in that the method comprises the association of a magnetisable particle with an ion channel, either directly or indirectly.

The method of the invention may comprise the manipulation of mammalian cells or other cell types, such as bacterial cells, plant cells, etc. However, it will be understood by the skilled man that the method of the present invention may be used to manipulate other cell types not mentioned herein. Furthermore, the method may be an in vitro method or an in vivo method, although an in vivo method is preferred Preferentially, the method of the invention comprises the remote manipulation of cells and/or of agonising or autagonising ion channels, e.g. manipulation from outside the body, i.e. remote mechanical activation.

The method of the invention may be utilised in relation to a variety of cells which are known per se. However, preferentially, the method is suitable for use with mammalian somatic cells, for example, bone, cartilage, muscle (skeletal and cardiac) lymphatic cells, endocrine cells, urinary system cells, cells relating to the reproduction system, neuronal cells and tumour cells.

The method of the invention may be utilised in connection with any conventionally known ion channels within the hereinbefore described. The method is especially suited for use in mechanosensitive ion channels. Such mechanosensitive ion channels have been identified in many cell types and have been predominantly described as calcium or potassium ion channels, although it should be understood that the method of the invention is not limited to use in relation to calcium or potassium ion channels. By way of example only, one such channel which has been well characterised at the molecular level and at the functional level in neuronal cells is the chromosomal gene TREK-1, which is part of the 2P K+ channel family. TREK-1 channels, have been identified in bone cells, and are known to respond to shear stress, cell swelling and membrane stretch as well as other external agents such as fatty acids and general anaesthetics.

A particular aspect of the present invention is to provide a method of manipulating mechanosensitive ion channels.

These "mechanosensitive" ion channels are present in a variety of mammalian, e.g. human, and bacterial cells and the present invention enables the cells to be selectively activated in the body and/or in cell cultures, see, for example, Sokabe, M, F Sachs, A Jing (1991) Quantitative video microscopy of patch clamped membranes: Stress, strain capacitance, and stretch channel activation. *Biophys J.* 59: 722-728; Stewart, Z, B Martinac and J Dobson (2000) Evidence for mechanosensitive transmembrane ion channels of small conductance in magnetotactic bacteria *Electro-and Magnetobiol.* 19: 81-89. As these channels are instrumental in normal cellular function and play a particularly important role in, for example, the production of bone and connective tissue or activation of the peripheral nervous system, the ability to manipulate them remotely, e.g. from outside the body, is especially advantageous an provides applications in, inter alia, pain relief, e.g. anaesthetics, therapeutics, tissue engineering and repair and cancer therapy.

In a further aspect of the invention the method may also be suitable for use with conventionally non mechanosensitive cells and/or ion channels by the transfection of channels into cells which may otherwise be otherwise non-responsive.

All ion channels open and close (i.e. change conformational state) in response to forces and this is the principle behind ion channel activation. In the case of mechanosensitive ion channels, the force results in membrane deformation, triggering the opening of the channel. Voltage-gated and ligand-gated ion channels are also "mechanoresponsive" in that they respond to mechanical stresses on the ion channel generated by coulomb forces (in the case of voltage-gated channels) and binding forces (in the case of ligand gated channels). As such, all ion channels can be activated by the method described herein provided that the magnetisable particle is coupled, either directly or indirectly, to the mechanoresponsive region of the channel protein.

Thus, in one aspect of the present invention the ion channel is a voltage-gated ion channel, alternatively, the ion channel is a ligand-gated ion channel.

A wide variety of particles may be used in the method of the invention. The magnetisable particle used in the method of the invention may be inherently magnetic or, alternatively, may be one which reacts in a magnetic field. Generally, any magnetic material may be used, however, by the term magnetic we mean, for example, a material which is paramagnetic superparamagnetic, ferromagnetic and/or antiferromagnetic, examples of which include elemental iron (Fe), or an compound, e.g. an iron salt, such as, magnetite ($Fe_3O_4$), maghemite ($\gamma Fe_2O_3$), and greigite ($Fe_3S_4$), or a chromium compound, e.g. a chromium salt, such as chromium oxide ($CrO_2$), or any combination thereof. Preferably the magnetic material comprises particles, e.g. nanoparticles, which comprises a magnetic core with a biocompatible coating. Thus, such preferred particles are nanoparticles and especially nanoparticles having a core and, e.g. a silica shell enveloping the core. However, also porous particles with multiple magnetic centres within the pores. An example of such particles are those nanoparticles described in U.S. Pat. No. 6,548,264 which is incorporated herein by reference. Thus, the prior art nanoparticles may have a mean size of less than 1 micron, each of said nanoparticles comprising (a) a core comprising a magnetisable particle and b) a silica shell enveloping the core, wherein the magnetisable particle is a magnetic material as hereinbefore described.

The micro- and nano-particles (intended to be attached to the cells) will generally be substantially spherical or elliptical. The size of the particles may vary according, inter alia, to the nature of the magnetisable material, the application, etc. However, an example of particles may be nanoparticles can having a mean size, e.g. diameter, of 5000 nm or less, e.g. from 1 nm to 5000 nm, preferably from 1 nm to 1000 nm, more preferably from 1 nm to 300 nm, or from 2 nm to 10 nm).

The particles for attachment to the cells may be coated or uncoated and single oz multi-domain. Examples of suitable particles include, but are not limited to:

(i) Coated magnetic microspheres (d=4 μm) available from Spherotech, Inc. These microspheres consist of a magnetically blocked core—coated by a polymer, (ii) Single-domain, ferrite-doped silica nanoparticles with tunable size (d=50-300 nm) and narrow size distribution.

In the method of the invention the ion channels may be activated by attaching the magnetisable particles as hereinbefore described to specific regions of the cellular membrane and/or to specific "receptors", on the ion channels themselves. Thus, the mechanical forces required to activate the channels can then be applied remotely by a magnetic field acting on these magnetic particles.

In particular the method of the invention comprises modifying a magnetisable particle as hereinbefore described by tagging the particle with one or more specific antibodies or protein binding motifs which recognise key cellular elements within a cell. These include transmembrane adhesion molecules, such as integrins, cadherins, selectins, and immunoglobulins or dispersed membrane adhesion proteins such as RGD (arginine-glycine-aspartate), see, for example, J. Chen, B. Fabry, E. L. Schiffrin, and N. Wang (2001) Twisting integrin receptors increases endothelin-1 gene expression in endothelial cells *Am J Physiol Cell Physiol*. 280: 1475-84; A. R. Bausch, U. Hellerer, M. Essler, M. Aepfelbacher, and E. Sackmann (2001) Rapid stiffening of integrin receptor-actin linkages in endothelial cells stimulated with thrombin: a magnetic bead microrheology study *Biophys J* 80: 2649-57; Catmell S H, J Dobson, S Verschueren, A El Haj (2002) Development of magnetic particle techniques for long-term culture of bone cells with intermittent mechanical activation *IEEE Transactions on NanoBioscience* 1: 92-97.

The method of the invention is especially advantageous because it provides a method of treatment of a variety of disorder. Indeed the invention provides a method of treatment which is applicable to any disorder in which one or more ion channels play a role. In addition, the invention provides a method for potential control of ion channel activation including pain relief, e.g. an anaesthetic role.

Thus according to the invention we provide a method of treatment of a patient suffering from a disorder in which an ion channel plays a role which comprises the administation to such a patient of magnetisable nanoparticles as hereinbefore described and manipulating those particles using a magnetic field.

The method of treatment as hereinbefore described should not be considered to be limited, but it is especially advantageous in tissue and/or bone repair. The method of treatment can be to facilitate further treatment by providing a method of pain relief e.g. for localised anaesthesia, to targeted regions of the body.

The nature of such cells may vary depending upon the nature of the tissue of interest. For example, the cells may be ligamentum cells for growing new ligaments, tenocytes for growing new tendon. Alternatively, the cells may be chondrocytes and/or other stromal cells, such as chondrocyte progenitor cells.

Thus the method of the invention may include the regeneration of tissue or the generation of artificial tissue, such as skin, cartilage, ligament, tendon, muscle or bone.

Alternatively the method may comprise wound healing and/oz tissue adhesion.

In a preferred embodiment the method may comprise bone repair and/or bone growth.

In a yet further alternative the method of the invention may include, for example, dental applications and/or veterinary applications.

The method also may be used as a mechanism for selectively killing cells (such as tumour cells) in vivo. In this case, magnetisable particles are attached to the target cell membrane or ion channel protein and a magnetic field is applied to the in vivo target region. The rapid, cyclic opening and closing (via the application of a time varying magnetic field), and/or the holding open (via the application of a static magnetic field) of ion channels in the cell membziae allows ions (such as $Ca^{++}$) to flood the cell, inducing osmotic shock and, consequently, cell death.

Thus, according to this aspect of the invention we also provide a method of destroying cells or inhibiting cell growth which comprises agonising or antagonising ion channels within a cell which by the association of a magnetisable particle with a cell.

The method may comprise a method of inducing osmotic shock to a cell, e.g. by agonising or antagonising ion channels within a cell by the association of a magnetisable particle with a cell. The method is especially useful in the treatment or alleviation of a tumour cell, e.g. a cancer cell.

Thus, the method may comprise the killing of cells by holding ion charnels open with a targeted static magnetic field. Alternatively, the method may comprise the killing of cells via cyclically opening and closing ion channels with a targeted, time-varying magnetic field.

In the methods of the invention the magnetic field may be varied depending upon, inter alia, the nature of the disorder to be treated, but may be, fox example, at a frequency of from 0.1 to 10 Hz. But, frequencies outside this range can also be used. The magnetic field will typically have a flux density in the order of (but not limited to) 10 mT to 1400 mT.

In the method of the invention the magnetic field may be generated outside the body for the case of in viva applications, and may be provided by a permanent magnet or an electromagnet. The magnetic field may be a constant or a variable field, e.g. a permanent magnet may be moved relative to the cells. In the case of an electromagnets a magnetic field may be generated by provision of appropriate electric current levels to the electromagnetic, optionally, in combination with alternating current.

According to a yet further aspect of the invention we provide a method of inducing a therapeutic effect in a cell which comprises agonising or antagonising ion channels within the cell by the association of a magnetisable particle with the cell and magnetically manipulating the magnetisable particle.

In addition we provide a method of treatment which comprises the administration of a therapeutically active agent which may be administered simultaneously, separately or sequentially with a magnetisable particle whilst agonising or antagonising ion channels within the cell.

We also provide a method of targeting a therapeutically active agent to a cell which comprises agonising or antagonising ion channels within the cell by the association of a magnetisable particle with the cell, magnetically manipulating the magnetisable particle and simultaneously, separately or sequentially administering the therapeutically active agent.

According to a yet further aspect of the invention we also provide the use of a magnetisable particle in a method of magnetically manipulating cells in vivo The use may comprise ex vivo manipulation of an in vivo process. Mole particularly, the invention provides the use of a magnetisable particle in the manufacture of a system for magnetically manipulating a cell which system comprises the association of a magnetisable particle with a cell and agonising or antagonising ion channels within the cell.

In this aspect of the invention the magnetisable particle may be associated directly with the cell. Alternatively, the use may comprise associating the magnetisable particle with an antibody, enzyme, etc., which is subsequently associated with the cell.

When the use of the invention comprises intracellular association. By way of example only, for TREK-1, the particle(s) may be associated with the N-terminus region of the ion channel. Alternatively, the particle(s) may be associated with the COOH terminus region of the ion channel.

The use of the invention may comprise the manipulation of mammalian cells or other cell types, such as bacterial cells, plant cells, etc. The use may be an in vitro use or an in vivo use, although an in vivo use is preferred.

Preferentially, the use of the invention comprises the remote manipulation of cells and/or of agonising or autagonising ion channels, e.g. manipulation from outside the body, i.e. remote mechanical activation.

The use of the invention may be utilised in relation to a variety of cells, which are known per se. However, preferentially, the use is suitable for use with mammalian somatic cells, for example, bone, cartilage, muscle (skeletal and cardiac) lymphatic cells, endocrine cells, urinary system cells, cells relating to the reproduction system, neuronal cells and tumour cells.

The use of the invention may be utilised in connection with any conventionally known ion channels within the cell, which is hereinbefore described. The use is especially suited for use in mechanosensitive ion channels hereinbefore described.

A particular aspect of the present invention is to provide the use in the manufacture of a system for manipulating mechanosensitive ion channels.

In a further aspect of the invention the use may also be suitable for use with conventionally non mechanosensitive cells and/or ion channels by the transfection of channels into cells which may otherwise be otherwise non-responsive.

In one aspect of the present invention the ion channel is a voltage-gated ion channel, alternatively; the ion channel is a ligand-gated ion channel.

A wide variety of particles may be used in the use of the invention. Generally, any magnetisable material may be used, examples of which include elemental iron (Fe), or an iron compound, e.g. an iron salt, such as, magnetic ($Fe_3O_4$), maghemite ($\gamma Fe_2O_3$), and greigite ($Fe_3S_4$), or a chromium compound, e.g. a chromium salt, such as, chromium oxide ($CrO_2$), or any combination thereof. Preferably the magnetic material comprises particles which comprises a magnetic core with a biocompatible coating. Thus, such preferred particles ae nanoparticles and especially nanoparticles having a core and, e.g. a silica shell enveloping the core. However, also porous particles with multiple magnetic centres within the pores. An example of such particles are those nanoparticles described in U.S. Pat. No. 6,548,264 which is incorporated herein by reference.

In a particular the use of the invention comprises modifying a magnetisable particle as hereinbefore described by tagging the particle with one or more specific antibodies or protein binding motifs which recognise key cellular elements within a cell. These include transmembrane adhesion molecules, such as integrins, cadherins, selectins, and immunoglobulins or dispersed membrane adhesion proteins such as RGD (arginine-glycine-aspartate).

The use of the invention is especially advantageous because it provides a system suitable for use in the treatment of a variety of disorders. Indeed the invention provides the use in the manufacture of a medicament suitable for a treatment, which is applicable to any disorder in which one or more ion channels play a role. In addition, the invention provides the use for potential control of ion charnel activation including pain relief, e.g. an anaestetic role.

Thus, according to the invention we provide the use of a magnetisable particle in the manufacture of a medicament suitable for the treatment of a patient suffering from a disorder in which an ion channel plays a role which comprises the administration to such a patient of magnetisable particles as hereinbefore described and manipulating those particles using a magnetic field.

The use as hereinbefore described should not be considered to be limited, but it is especially advantageous in tissue and/or bone repair. The use can be to facilitate further treatment by providing a method of pain relief, e.g. for localised anaesthesia, to targeted regions of the body.

The nature of such cells may vary depending upon the nature of the tissue of interest. For example, the cells may be ligamentum cells for growing new ligaments, tenocytes for growing new tendon. Alternatively, the cells may be chondrocytes and/or other stromal cells, such as chondrocyte progenitor cells.

Thus, the use may include the regeneration of tissue or the generation of artificial tissue, such as skin, cartilage, ligament, tendon, muscle or bone.

Alternatively the use may comprise wound healing and/or tissue adhesion.

In a preferred embodiment the use may comprise bone repair and/or bone growth.

In a yet further alternative the use of the invention may include, for example, dental applications and/or veterinary applications.

The use also may be used as a mechanism for selectively killing cells (such as tumour cells) in vivo as hereinbefore described.

Thus, according to this aspect of the invention we also provide the use of a magnetisable particle in the manufacture of a system for destroying cells or inhibiting cell growth which comprises agonising or antagonising ion channels within a cell which by the association of a magnetisable particle with a cell.

The use may comprise use in a method of inducing osmotic shock to a cell, e.g. by agonising or antagonising ion channels within a cell by the association of a magnetisable particle with a cell. The use in this aspect of the invention is especially useful in the treatment or alleviation of a tumour cell, e.g. a cancer cell.

Thus, the use may comprise the holding of cells by holding ion channels open with a targeted static magnetic field. Alternatively, the use may comprise the killing of cells via cyclically opening and closing ion channels with a targeted, time-varying magnetic field.

According to a yet further aspect of the invention we provide the use of a magnetisable particle in the manufacture of a system for inducing a therapeutic effect in a cell which comprises agonising or antagonising ion channels within the cell by the association of a magnetisable particle with the cell and magnetically manipulating the magnetisable particle.

In addition we provide the use of a magnetisable particle in the manufacture of a system comprising a therapeutically active agent which may be administered simultaneously separately or sequentially with the magnetisable particle whilst agonising or antagonising ion channels within the cell.

We also provide the use of a magnetisable particle in the manufacture of a system for targeting a therapeutically active agent to a cell which comprises agonising or antagonising ion channels within the cell by the association of a magnetisable particle with the cell, magnetically manipulating the magnetisable particle and simultaneously, separately or sequentially administering the therapeutically active agent.

According to a yet further aspect of the invention we provide a kit comprising a therapeutically active agent and means for associating a magnetisable particle with a cell.

It will be understood by the skilled that any conventionally known therapeutically active agent or a combination of therapeutically active agents may be utilised in the kit of the invention.

Thus, the kit may comprise a vessel containing a therapeutically active agent, a source of magnetisable particles and instructions for the simultaneous, sequential or separate administration thereof. The kit of the invention may also include other agents known per se. The invention may also include the use of skit as hereinbefore described in the manufacture of a medicament.

BRIEF DESCRIPTION OF THE FIGURES

The invention will now be described by way of example only and with reference to the accompanying drawings in which FIG. 1a) is a schematic representation of the structure of TRK-1 showing the three sites of 12× histidine insertions for tagging magnetic beads for mechanical manipulation;

FIG. 2 is a schematic of the TREK ion channel showing structure and location of the His tags present in the protein. Red circles indicate the sites of the His tags at the three sites, the primary loop, the COOH terminus and the NH terminus;

FIG. 3 is a representation of the magnetic activation of Trek-1 monitored via downstream changes in intracellular calcium.

DETAILED DESCRIPTION

EXAMPLE 1

Activation of TREK-1 Using Magnetic Cytometry

The modified TREK-1 gene was transvected into the human HEK 293 cell line. Detection of plasmid transfection efficiency was conducted by monitoring CD8 expression using immunocytochemistry, electrophysiology using whole cell recordings and a fluorescent marker for membrane depolarisation monitored via confocal microscopy. Three regions of the molecule were tagged for experimental manipulation by insertion for a 12× histidine coding sequence as shown in FIG. 1a. Functionalised, magnetic micro- and nano-particles were coupled to the cell membrane using the 12× His antibody coatings to enable force to be applied to different regions of the channel. Particles were twisted by moving high-field rare earth magnets (NdFeB) magnets with surface flux density of up to 1.4 Tesla, about a vertical axis near the cell culture. During this process, cells were monitored via phase contrast microscopy and confocal microscopy. Electrical activity in cells were monitored using whole cell recordings.

Specific monoclonal antibodies raised to the three regions prior to histidine insertions outlined above have been raised for tagging endogenous TREK channels in vivo.

EXAMPLE 2

Non-Specific Membrane Deformation Using Magnetic Cytometry

Figure 1B:
FIG. 1b) illustrates primary human astrocytes with membrane bound RGD coated carboxyl ferromagnetic particles (4 μm) (magniication×1000)
Figure 1A:
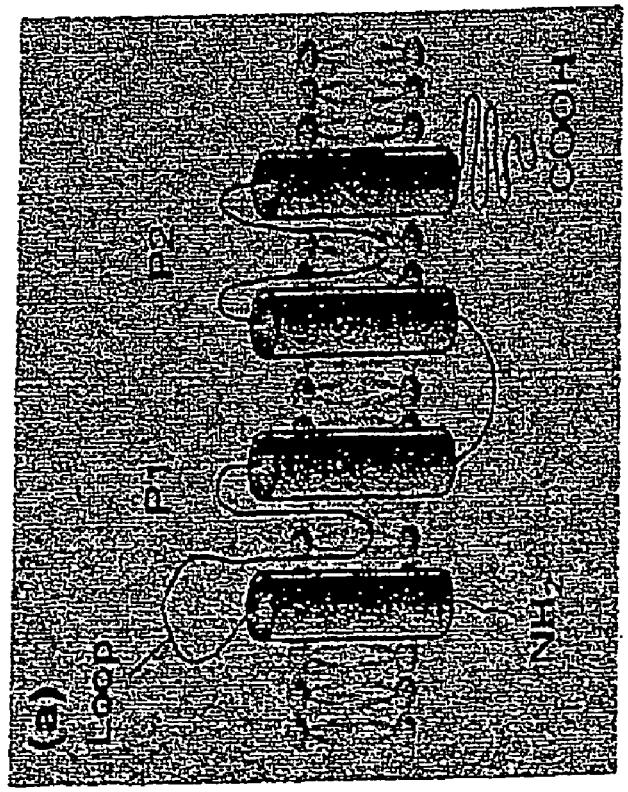

Biocompatible magnetic micro- and nanoparticles were coupled to the cell membrane (specifically with monoclonal antibodies to RGD containing peptides and collagen) to stretch generalised regions of the cell (FIG. 1b). The torque applied to magnetically blocked particles deforms the cell membrane and activates nearby MS ion channels following application of a range of magnetic fields. In addition, the cells were biochemically assayed to determine whether reaction pathways are being initiated by magnetic twisting (e.g. prostaglandin and extracellular matrix production). MS ion channel blockers such as gadolinium or amiloride were added extracellularly to confirm whether the MS channels are instrumental in any observed changes.

Initial experiments employed functionalised magnetic microspheres (d=4 μm) available from Spherotech. Inc. In addition magnetically blocked, ferrite-doped silica nanoparticles with tunable size (d=50-300 m) and narrow size distribution and PVA/magnetite nanoparticle-based ferrofluids (d=4-10 nm) were synthesised. High-field rare earth magnets again were used to generate the applied fields.

EXAMPLE 3

Magnetic Activation in a 3D Model

The use of magnetic strategies for spatially targeted ion channel activation in a 3D, cell-seeded scaffold was investigated by applying a magnetic field across a cell-seeded construct within a bioreactor. The ion channels in the cells were activated within the scaffold and the long-term effects of this ion channel activation on mat synthesis and cell proliferation assessed. Magnetic particle-based approaches with a non-specific activation and a TREK-transfected bone and cartilage cell lined model were used.

EXAMPLE 4

Calcium Channel Activity Following Attachment of Magnetic Particles to Anti-His Antibody COS-7 cells were co-transfected with FLASH-pericam and 6His. TREK-1. 1 μm anti-His antibody coated superparamagnetic particles were then attached to the surfaces of transfected cells and manipulated by the application of a magnetic field (750 G). Flash pericam was used to monitor changes in intracellular calcium activity following the magnetic activation and subsequent exposure to 100 μm Riluzole, a chemical activator of TREK-1.

Referring to FIG. 3, COS-7 cells weie co-transfected with 'Flash' pericam and 12His Trek-1—Red and yellow lines indicate the cells with magnetic particles attached. Green and White lines indicate the cells without magnetic particles attached. The Magnetic field applied for 1 sec—yellow arrow Application of 100 uM Riluzole to the culture media—red arrow.

Figure 4:
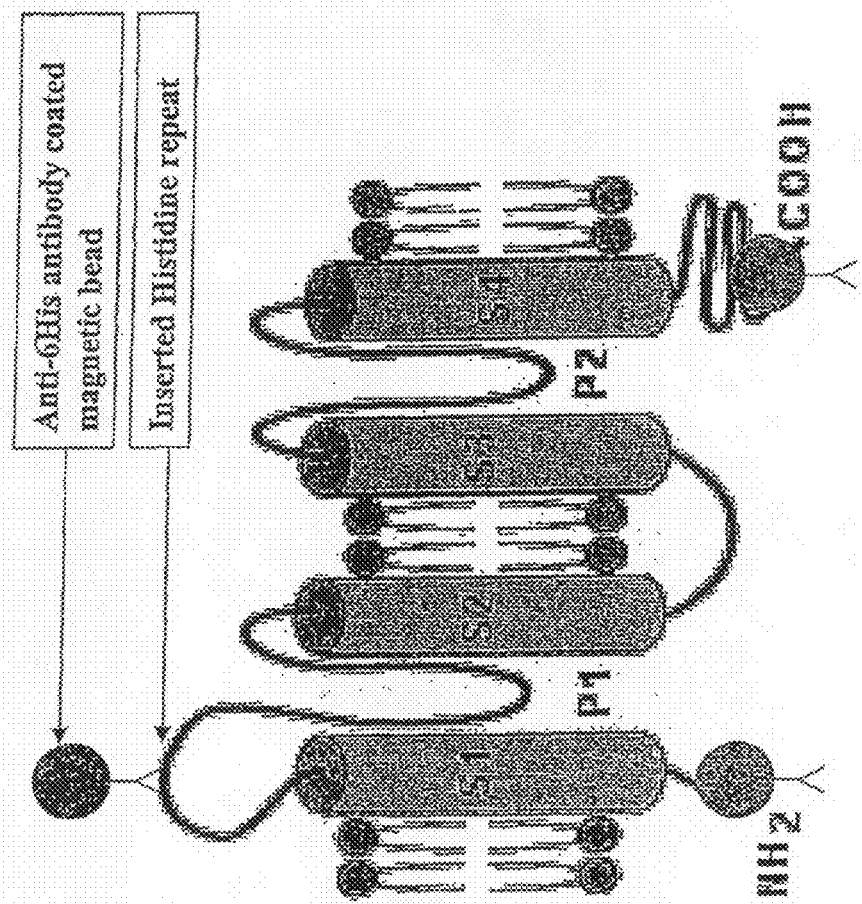
FIG. 4 is a representation of the magnetic activation of TREK-1 induces transient rise in intracellular calcium in HEK293 T cells co-transfected with and Flashpericam.

Referring to FIG. 4, Channel 1=Green=HEK293 cells with magnetic particle attached=white arrow indicates calcium=response, Channel 2=demonstrates movement of the particles attached to the cells following application of the magnet (indicated by a red arrow).

The invention claimed is:

1. An in vitro method for the generation of cartilage tissue from mammalian chondrocyte progenitor cells expressing mechanosensitive TWIK-related potassium (TREK) ion channels, the method comprising:
   (i) providing mammalian chondrocyte progenitor cells in culture in vitro, wherein the cells express mechanosensitive TREK ion channels;
   (ii) providing magnetizable particles comprising a magnetic core and biocompatible coating, wherein the magnetizable particles are tagged with one or more antibodies specific for said TREK ion channels;
   (iii) contacting said cells with said magnetizable particles and allowing the magnetizable particles to couple with said TREK ion channels;

(iv) applying a magnetic field to said cells, the magnetic field thereby applying mechanical force to said magnetizable particles;

the method thereby generating cartilage tissue.

2. The method of claim 1 wherein said TREK ion channel is TREK-1.

3. The method of claim 1 wherein the magnetic field is a variable magnetic field having a frequency of from 0.1 to 10 Hz.

4. The method of claim 1 wherein the magnetic field has a flux density of 10 mT to 1400 mT.

5. The method of claim 1 wherein the magnetizable particles have a mean size of 5000 nm or less.

6. The method of claim 1 wherein the magnetizable particles comprise elemental iron (Fe), or a compound thereof.

7. The method of claim 6 wherein the iron compound is an iron salt selected from the group consisting of: magnetite ($Fe_3O_4$), maghemite ($\gamma Fe_2O_3$), greigite ($Fe_3S_4$), and combinations thereof.

8. The method of claim 1 wherein the magnetizable particles comprise a chromium compound.

9. The method of claim 8 wherein the chromium compound is chromium oxide ($CrO_2$).

10. A method for the generation of new cartilage tissue in a patient, wherein the new cartilage tissue is generated from chondrocyte prqgenitor cells expressihg mechanosensitive TWIK-related potassium (TREK) ion channels, the method comprising:
(i) providing magnetizable particles comprising a magnetic core and biocompatible coating, wherein the magnetizable particles are tagged with one or more antibodies specific for said TREK ion channel;
(ii) administering said particles to a mammalian patient in need of generation of new cartilage tissue, wherein said particles are administered to a site in the patient at which new cartilage tissue is required to be generated and at which chondrocyte progenitor cells expressing the mechanosensitive TREK ion channel are present, and allowing the magnetizable particles to couple wit said TREK ion channels;
(iii) applying a magnetic field to said cells, the magnetic field thereby applying mechanical force to magnetizable particles in the body of the patient;

the method thereby generating new cartilage tissue at said site.

11. The method of claim 10 wherein the method involves wound healing in the patient through the generation of new cartilage tissue.

12. The method of claim 10 wherein said TREK ion channel is TREK-1.

13. The method of claim 10 wherein the magnetic field is a variable magnetic field having a frequency of from 0.1 to 10 Hz.

14. The method of claim 10 wherein the magnetic field has a flux density of 10 mT to 1400 mT.

15. The method of claim 10 wherein the magnetizable particles have a mean size of 5000 nm or less.

16. The method of claim 10 wherein the magnetizable particles comprise elemental iron (Fe), or a compound thereof.

17. The method of claim 16 wherein the iron compound is an iron salt selected from the group consisting of: magnetite ($Fe_3O_4$), maghemite ($\gamma Fe_2O_3$), greigite ($Fe_3S_4$, and combinations thereof.

18. The method of claim 10 wherein the magnetizable particles comprise a chromium compound.

19. The method of claim 18 wherein the chromium compound is chromium oxide ($CrO_2$).

* * * * *

UNITED STATES PATENT AND TRADEMARK OFFICE
CERTIFICATE OF CORRECTION

PATENT NO. : 7,625,562 B2
APPLICATION NO. : 10/518956
DATED : December 1, 2009
INVENTOR(S) : Alicia Jennifer Hafeeza El Haj and Jon Paul Dobson It is certified that error appears in the above-identified patent and that said Letters Patent is hereby corrected as shown below:

| Col. No. | Line(s) | Edits |
|---|---|---|
| 12 | 4 | Replace "to couple wit said" with --to couple with said-- |
| 12 | 28-29 | Replace "greigite ($Fe_3S_4$, and combinations thereof" with --greigite ($Fe_3S_4$), and combinations thereof-- |

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,625,562 B2 Page 1 of 1
APPLICATION NO. : 10/518956
DATED : December 1, 2009
INVENTOR(S) : El Haj et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 176 days.

Signed and Sealed this

Twenty-first Day of December, 2010

David J. Kappos
*Director of the United States Patent and Trademark Office*